(12) United States Patent
Fountain

(10) Patent No.: US 8,597,678 B2
(45) Date of Patent: Dec. 3, 2013

(54) NANOLIPIDIC PARTICLES

(75) Inventor: Michael W. Fountain, Tampa, FL (US)

(73) Assignee: Dermazone Solutions, Inc., St. Petersburg, FL (US)

( * ) Notice: Subject to any disclaimer, the term of this patent is extended or adjusted under 35 U.S.C. 154(b) by 566 days.

(21) Appl. No.: 11/644,281

(22) Filed: Dec. 22, 2006

(65) Prior Publication Data

US 2007/0154539 A1  Jul. 5, 2007

Related U.S. Application Data

(60) Provisional application No. 60/755,171, filed on Dec. 30, 2005.

(51) Int. Cl.
*A61K 8/14* (2006.01)
*A61K 9/127* (2006.01)

(52) U.S. Cl.
CPC . *A61K 9/127* (2013.01); *A61K 8/14* (2013.01); *A61K 9/1271* (2013.01); *Y10S 977/906* (2013.01); *Y10S 977/907* (2013.01); *Y10S 977/797* (2013.01)
USPC ........... 424/450; 977/797; 977/906; 977/907; 977/797

(58) Field of Classification Search
None
See application file for complete search history.

(56) References Cited

U.S. PATENT DOCUMENTS

| | | | |
|---|---|---|---|
| 5,009,819 A * | 4/1991 | Popescu et al. | 264/4.1 |
| 5,269,979 A | 12/1993 | Fountain | |
| 5,437,274 A | 8/1995 | Khoobehi et al. | |
| 5,716,638 A * | 2/1998 | Touitou | 424/450 |
| 5,814,343 A * | 9/1998 | Jones et al. | 424/499 |
| 5,879,703 A | 3/1999 | Fountain | |
| 5,885,921 A | 3/1999 | Krupey | |
| 6,096,331 A | 8/2000 | Desai et al. | |
| 6,203,778 B1 * | 3/2001 | Brasch | 424/9.411 |
| 2001/0006643 A1 * | 7/2001 | Hope | 424/400 |
| 2003/0091621 A1 * | 5/2003 | Tardi et al. | 424/450 |
| 2005/0191330 A1 * | 9/2005 | Huglin et al. | 424/401 |

FOREIGN PATENT DOCUMENTS

WO  WO 9916426  4/1999

OTHER PUBLICATIONS

JR Philippot, F Schuber. "Liposomes as Tools in Basic Research and Industry." CRC Press, 1995, pp. 7-8.*
G Masson. "Characterization of Small Lipid Vesicles Prepared by Microfluidization." Progress in Colloid & Polymer Science. vol. 79, 1989, pp. 49-51.*
B Godin, E Touitou. "Ethosomes: New Prospects in Transdermal Delivery." Critical Reviews in Therapeutic Drug Carrier Systems. vol. 20(1), 2003, pp. 63-102.*
JY Zheng, M-y Fulu, DY Lee, TE Barber, AL Adjei. Pulmonary Peptide Delivery: "Effect of Taste-Masking Excipients on Leuprolide Suspension Metered-Dose Inhalers." Pharmaceutical Development and Technology, vol. 6(4), 2001, pp. 521-530.*
ND Santos, KA Cox, CA McKenzie, FV Baarda, RC Gallagher, G Karlsson, K Edwards, LD Mayer, C Allen, MB Bally. "pH gradient loading of anthracyclines into cholesterol-free liposomes: enhancing drug loading rates through use of ethanol." Biochimica et Biophysica Acta, vol. 1661, 2004, pp. 47-60.*
RH Muller, K Mader, S Gohla. "Solid lipid nanoparticles (SLN) for controlled drug delivery—a review of the state of the art." European Journal of Pharmaceutics and Biopharmaceutics, vol. 50, 2000, pp. 161-177.*
International Preliminary Report on Patentability for corresponding Application PCT/ US2006/048770; Jan. 29, 2008.
Berger, et al., "Filter extrusion of liposomes using different devices: comparisons of liposome size, encapsulation efficiency, and process characteristics," Int J Pharm, vol. 223, n.1-2 (2001), pp. 55-68.

\* cited by examiner

*Primary Examiner* — Frederick Krass
*Assistant Examiner* — Isaac Shomer
(74) *Attorney, Agent, or Firm* — D. Scott Hemingway; Hemingway & Hansen, LLP

(57) ABSTRACT

Nanolipidic Particles (NLPs) having average mean diameters of 1 nm to 20 nm are made from a precursor solution. NLPs can be loaded with a desired passenger molecule. Assemblies of these particles, called NLP assemblies, result in a vehicle population of a desired size. Single application or multifunction NLP assemblies are made from the loaded NLPs and range in size from about 30 to about 200 nm. A method of using preloaded NLPs to make larger carrier vehicles or a mixed population provides increased encapsulation efficiency. NLPs have application in the cosmetics, pharmaceutical, and food and beverage industries.

39 Claims, No Drawings

US 8,597,678 B2

NANOLIPIDIC PARTICLES

CROSS REFERENCE TO RELATED APPLICATIONS

This application claims the benefit of U.S. Provisional Application No. 60/755,171 filed Dec. 30, 2005.

STATEMENT REGARDING FEDERALLY SPONSORED RESEARCH OR DEVELOPMENT

Not applicable.

TECHNICAL FIELD OF INVENTION

This invention concerns the field of incorporating passenger molecules in lipid vesicles.

BACKGROUND OF THE INVENTION

Incorporating passenger molecules, such as pharmaceutical active ingredients, in lipid vesicles such as liposomes has been reported in the prior art. An amphipathic carrier structure denoted as a Solvent Dilution Microcarrier ("SDMC") was disclosed in U.S. Pat. No. 5,269,979. In general, the '979 patent described making a plurality of SDMC vehicles by solubilizing an amphipathic material and a passenger molecule in a first quantity of a non-aqueous solvent. Following this, a first quantity of water was added, forming a turbid suspension. In a subsequent step, a second quantity of non-aqueous solvent was added to form an optically clear solution. The final step of a preferred embodiment was to organize the optically clear solution into SDMC vehicles by mixing with air or a second quantity of water.

In U.S. Pat. No. 5,879,703, a method for preparing a shelf-stable precursor solution useful for remote encapsulation of active ingredients was described. In '703, the precursor solution was made by solubilizing an amphipathic material in a non-aqueous solvent. A quantity of water was added to the first mixture to form a precursor solution characterized by optical clarity and being monophasic at room temperature. The precursor solution could be stored for an extended period of time—and the desired active ingredient added at a later time, perhaps at a remote location, to form a loaded precursor solution. SDMCs could be formed, in preferred embodiments, from the loaded precursor solution by diluting with water or mixing with air. SDMCs ranged from about 230 to about 412 nanometers in size.

Although SDMCs and the shelf-stable precursor solution provided for making vehicles suitable for delivering active ingredients in a variety of applications, a need remained for improved vehicles for delivery of passenger molecules.

It has now been found that the shelf-stable precursor solution such as described in the '703 patent can be used as a starting material in a novel method which results in vehicles of a smaller size than previously reported. The starting material is manipulated by dilution with a non-aqueous solvent, either before or after loading with a passenger molecule, to provide one or more defined populations of nanolipidic particles ("NLPs") which range in size from about 1 nanometer to about 20 nanometers. NLP assemblies are formed from the NLPs which range in size from about 30 nanometers to about 200 nanometers. In addition, it has been found that NLPs can be used in a method for making carrier vehicle preparations which are mixed smaller and larger carrier vehicles, or having a larger mean size of about 200-300 nanometers, but improved encapsulation of passenger molecules.

DETAILED DESCRIPTION

Nanolipidic particles ("NLP"s) according to the present invention have a size range of from about 1 to about 20 nanometers, as measured by a standard laser light scattering technique, discussed in detail herein. Various subpopulations of NLPs may be made. The preferred distinct subpopulations of NLPs range in size from about 1 to about 4 nm, from about 4 to about 7 nm, from about 7 to about 10 nm, from about 10 to about 14 nm, from about 14 to about 18 nm, and from about 18 to about 20 nm. A preferred subpopulation comprises NLPs having an average size of about 9 to 10 nanometers.

NLPs are made from a precursor solution as described in U.S. Pat. No. 5,879,703, which is herein incorporated by reference as if fully set forth herein. As stated in the '703 patent, a precursor solution may be made by solubilizing an amphipathic material in a first quantity of a non-aqueous solvent appropriate to solubilize the amphipathic material to form a first mixture. The amphipathic material preferably comprises phospholipids (PL). A preferred PL comprises one or more of the following phosphatides: phospatidylcholine (PC), phospatidylethanolamine (PE), phosphatidic acid (PA) and phosphatidylinositol (PI). In a preferred embodiment, PC, PE, PA and PI are combined. A preferred ratio of PLs useful in the invention is PC:PE:PA:PI of 6.5:2.5:0.7:0.3 in ethanol. Preferably, one gram of PL is solubilized in 5.0-7.5 ml of ethanol solvent.

After dissolution of the amphipathic material, a quantity of water is added to form a turbid suspension. The amount of water to add is approximately 9 kg to 31 kg of dissolved amphipathic material, but can be varied to result in the desired turbid suspension. A second quantity of non-aqueous solvent, such as ethanol, is added until the turbid suspension is monophasic and has optical clarity at room temperature. This resulting product is a precursor solution which is shelf-stable over time.

In the '703 patent, it was disclosed that a precursor solution made according to the process disclosed therein was shelf stable at least up to two years, and perhaps longer, as long as it remains in a monophasic condition. It has been recently determined that precursor solutions made by this method are stable for at least eight years, independent of manufacturing, location, season, year and lot.

It has now been found that a precursor solution such as disclosed in '703 can be used as a starting material to make nanolipidic particles (NLPs) and NLP assemblies. In '703, the precursor solution was disclosed as being useful for making SDMCs at a later point in time and, perhaps, a remote location. SDMCs have a diameter of from about 230 to about 412 nm. In contrast, NLPs have a mean diameter of from about 1 nm to about 20 nm and NLP assemblies have a mean diameter from about 30 nm to about 200 nm.

Various populations of NLP assemblies may be made for various applications. Preferred populations range from about 40-60 nm; about 60-80 nm; about 80-110 nm; about 110-140 nm; and about 150-200 nm. NLP assembly populations are generally 20-30% smaller in diameter than SDMCs for the same passenger molecule.

A slightly larger population or mixed population of carrier vehicles is referred to herein as ECVs or encapsulating carrier vehicles. Although overlapping the mean diameter of SDMCs, the ECV is made using a different method employing NLPs and the result is a carrier vehicle population which has been found to exhibit a higher encapsulating efficiency. The ECVs are described as having a mean diameter from about 200 nm to 300 nm.

To make carriers for passenger molecules according to the disclosed method, such as NLP populations, NLP assemblies, or ECVs, the precursor solution as previously described in the '703 patent is diluted with a suitable solvent or mixed solvent system which is compatible with the solvent system used in the precursor solution. This dilution is performed either before or after addition of the passenger molecule as will be further described in detail below. The solvent is selected for biocompatibility if the end use of the carriers will require that characteristic. The solvent or mixed solvent system used for dilution must be miscible with the solvents in the precursor solution and should be effective to disperse rather than dissolve the carriers. Most preferably, the solvent used for dilution is ethanol, since it possesses the desired qualities. The dilution is preferably conducted in a sequential or serial manner. For example, a first dilution of 1:10 provides a population of carriers, and further serial dilution to about 1:0.5 provides a series of populations of carriers. The size of the carriers in each dilution can be determined by laser light scattering. Mixed populations of NLPs and larger vesicles may be created at lower dilutions with the non-aqueous solvent. An appropriate instrument for this purpose is the Zetasizer 1000 manufactured by Malvern Instruments, (Worcestershire United Kingdom). Diameters of particles reported herein were determining using the Multimodal Analysis Mode of the Zetasizer 1000 to determine particle size by peak intensities. Other techniques may be used to analyze particle size, which results can be correlated to the numerical values obtained with the light scattering technique described herein.

Addition of the desired passenger molecule occurs prior to dilution with the solvent if the passenger molecule is lipophilic or amphipathic. Addition occurs after dilution of the passenger molecule is water soluble.

Thus, in the case of a lipophilic or amphipathic passenger molecule, the NLP loaded populations form upon dilution with the solvent. NLP assembly populations or ECVs are formed by dilution of the NLP loaded population into water.

In the case of a water soluble passenger molecule, the precursor solution is mixed with a passenger molecule dissolved in water. NLP assembly populations or ECVs are formed upon dilution with the non-aqueous solvent. If a serial dilution technique is used, distinct populations are formed.

Based on curves observed from different classes of compounds, ranges for the finished NLP assembly population can be established for each NLP population used to form the final NLP assembly population. The more non-aqueous solvent that is used to dilute the NLPs, the smaller the NLP assembly populations.

Various NLP loaded populations may be mixed and matched to provide a multifunctional NLP assembly product. As just one example, in a skin care product, it might be desired to topically provide Vitamin E and an antibiotic in a single preparation. The different NLP loaded populations within the NLP assembly could provide a preparation which allows one active ingredient to be preferentially absorbed over the other, thus allowing a control of the rates of penetration of different ingredients in a single preparation. Alternatively, a single NLP population could be loaded with more than one passenger molecule to provide the multifunctionality.

An injectable multifunctional NLP assembly product could also provide advantages: Due to the novel ability of this invention to produce well defined populations of extremely small (sub 150 nm) populations, NLP products may be able to be produced which have greatly increased serum half-lives. Such particles may be able to evade initial uptake by the body's immune system and possibly aid in the delivery of drug payloads to cells and tissues not easily accessed by normal vascular delivery mechanisms; i.e. trans blood-brain barrier delivery and extra-vascular delivery of drug payloads to selected or targeted organs and tissues.

The ability to select an NLP population of a preferable size for a given application provides advantages to the manufacturing process as well. Less material will be required to form the end product if an NLP precursor solution is selected for a particular size need. Loading efficiency also goes up. The number of NLP particles increases as the size of the NLP populations decreases as a function of the decreasing diameter of the spherical NLP product (assuming the amount of lipid to passenger molecule remains constant). This may provide a higher concentration of passenger molecule per unit volume.

Another advantage to the NLP technology is that an optically clear solution containing NLPs loaded with passenger molecules can be made by selecting conditions where the NLPs are less than about 150 nm in size. It is many times important that a product appear optically clear or it will fail to gain consumer acceptance. For example, loaded NLPs in an optically clear solution have application in the beverage industry and the pharmaceutical industry for liquid products. As one example, a mouthwash can be prepared that contains NLPs which encapsulates an ingredient for time-release in the mouth. A consumer prefers to purchase an optically clear mouthwash rather than a cloudy one.

The passenger molecules suitable for use in forming a NLP loaded population are numerous. In one embodiment, passenger molecules can be selected which exhibit lipid solubility or are amphipathic. These molecules have solubility profiles ideally suited for loading into NLPS. In another embodiment, water soluble molecules may be incorporated into NLPs by solubilization into the aqueous solution used to form the finished NLP product. Using these two approaches virtually any molecule may be incorporated as a passenger molecule into NLP products of defined sizes. An innovative use of both approaches may be used to incorporate both lipid and water soluble compounds into a NLP assembly product by first incorporating lipid soluble compounds into NLPs prior to dilution with ethanol and second incorporating water soluble molecule(s) into the water solution used to form the finished NLP product of defined size.

Numerous passenger molecules have been incorporated into NLPs. For example, fat-soluble vitamins may be used as a passenger molecule. Vitamins D, E and K have been found to be appropriate for NLPs.

Water soluble vitamins, such as Vitamin B and C may also be used as passenger molecules. Both water soluble and fat soluble vitamins may be combined in an NLP assembly if it is desired that both be administered by using the technique discussed above.

Passenger molecules such as are useful in sunscreens may also be used. Benzophenone (UVB and UVA absorber), for example, can be appropriately used as an NLP passenger molecule.

Other preferred passenger molecules are antibiotics such as aminoglycosides (Gentamycin), beta-lactams (Penicillin G) and macrolides (Erythromycin). Anesthetics such as lidocaine have been effectively incorporated in NLPs, as have steroids and antifungals (griseofulvin).

NLPs may also be used in the food and beverage industry. For example, NLPs incorporating caffeine may be used in dietary supplements for appetite suppression. Encapsulation in NLPs has been found to be effective to mask the taste of the passenger molecule if it is desired that tasting of such be bypassed upon ingestion.

Another application in the food and beverage industry is the incorporation of substances into NLPs which will be tasted, rather than masked. Flavorings such as peppermint oil and other oils are appropriately incorporated into NLPs The encapsulation of oil-containing substances may lead to increased shelf life in that the encapsulated substance is protected from oxidation. In addition, the encapsulation of substances would permit additional options for manufacturers and consumers. As just one example, a manufacturer of a beverage could prepare and bottle one base flavor. The consumer would then have the option of adding NLP packets to the beverage to meet the taste preferences of the consumer or to enrich it with vitamins. A consumer that prefers a strong peppermint flavoring in a chocolate drink could add NLPs containing peppermint oil to his or her beverage. Substances that are meant to be tasted can also be loosely associated with the exterior of the NLP by providing such substances in the aqueous phase of the procedure. For example, an NLP containing a vitamin that preferably should not be tasted can have a pleasant taste on the outside thereof. If it is desired that the NLPs remain in the mouth so that their contents can be tasted, a natural carbohydrate or sugar can be linked to the NLP by merely providing it in the aqueous solution. This will stick to the inside of the mouth for a period of time, and normal mouth chemistry and mastication will release the contents of the NLPs to provide the desired effect. The NLPs can also be subjected to agitation and shear such as in a blender or heavy industrial equipment at a manufacturing site to provide flavorings to foods and beverages.

NLPs may also be used for incorporation of peptides. Tripeptides, Tetrapeptides, Hexapeptides and Nonapeptides have been effectively incorporated into NLPs.

NLPs may also be useful in industries requiring dye as an ingredient. Water soluble and lipid soluble dyes may be used.

NLPs may be used to incorporate oils of various types, such as essential oils and scented oils, into products. Examples of such products are lotions, emulsions, creams, cosmetics, cosmeceuticals and perfumes. The NLPs may be loaded with the oils and provide a time-release function to the product, allowing the desired ingredient to be released over a period of time. For example, the scent of a perfume could be incorporated in one or more size populations of NLPs and the scent released over a longer period of time than scent not incorporated in NLPs.

If the desired passenger molecule is water soluble, the passenger molecule should first be dissolved in water. The incorporation step, or loading of the passenger molecule into the NLP, is accomplished when the NLP product is formed by adding the dissolved passenger molecule to the precursor solution.

Example 1

Use of Shelf-Stable Precursor Solution as a Starting Ingredient for Nanolipidic Particles Shelf-Stable Precursor Solution (Manufacturing Lot 0013-040010) was used to prepare NLPs of a variety of defined size populations. Using the Malvern Laser Light Scattering instrument (Zetasizer 1000) nascent populations of NLP were measured to be 9 nm. To prepare NLP assembly populations of defined sizes, the following procedure was followed: 1 ml aliquots of Stock Precursor Solution (Lot 0013-040010) were placed in 10 ml test tubes. To prepare defined populations of NLP product various amounts of ethanol were added to each of the sample preparations. Following formation of the NLP preparations, 1 ml aliquots of each sample were added to 20 ml of distilled water using a 2 ml pipette. Each preparation was stirred at room temperature for 5 minutes and then 2 ml aliquots were removed, vortexed for 20 seconds and then subjected to size analysis using the Malvern Laser Light Scattering instrument. The results are shown in Table 1.

TABLE 1

| Stock Precursor Solution | Ethanol | No Passenger | Size |
| --- | --- | --- | --- |
| 1 ml | 0 ml | [Control] | 278 nm |
| 1 ml | 0.2 ml | [Mixed Population] | 242 nm |
| 1 ml | 0.5 ml | [NLP Assembly] | 186 nm |
| 1 ml | 0.8 ml | [NLP Assembly] | 160 nm |
| 1 ml | 1.0 ml | [NLP Assembly] | 138 nm |
| 1 ml | 2.0 ml | [NLP Assembly] | 110 nm |
| 1 ml | 3.0 ml | [NLP Assembly] | 98 nm |
| 1 ml | 5.0 ml | [NLP Assembly] | 61 nm |
| 1 ml | 10 ml | [NLP Assembly] | 34 nm |

Example 2

Nanolipidic Particles with Lipid-Soluble Passenger Molecules

Shelf-Stable Precursor Solution (Manufacturing Lot 0013-040010) was used to prepare NLPs of a variety of defined size populations. Using the Malvern Laser Light Scattering instrument (Zetasizer 1000) nascent populations of NLP were measured to be 9 nm. To prepare NLP populations with Vitamin K1 of defined sizes the following procedure was followed: To 10 ml of Shelf-Stable Stock Solution (Lot 0013-040010) was added 10 mg of Vitamin K1. The material was solubilized by vortexing yielding a loaded NLP preparation with an effective concentration of 1 mg/ml of Vitamin K1. 1 ml aliquots of The Vitamin K1 Loaded NLPs were placed in 10 ml test tubes. To prepare defined populations of NLP product various amounts of ethanol were added to each of the sample preparations. Following formation of the NLP preparations, 1 ml aliquots of each sample were added to 20 ml of distilled water using a 2 ml pipette. Each preparation was stirred at room temperature for 5 minutes and then 2 ml aliquots were removed, vortexed for 20 seconds and then subjected to size analysis using the Malvern Laser Light Scattering instrument. The resulting Vitamin K1 preparations are shown in Table 2.

TABLE 2

| Stock Precursor Solution | Ethanol | Vitamin K1 | Size |
| --- | --- | --- | --- |
| 1 ml | 0 ml | [Control] | 271 nm |
| 1 ml | 0.5 ml | [Mixed Population] | 229 nm |
| 1 ml | 1.0 | [NLP Assembly] | 76 nm |
| 1 ml | 2.0 | [NLP Assembly] | 51 nm |
| 1 ml | 5.0 | [NLP Assembly] | 40 nm |
| 1 ml | 10.0 | [NLP Assembly] | 30 nm |

Example 3

NLPs with Water Soluble Passenger Molecules

Shelf-Stable Precursor Solution (Manufacturing Lot 0013-040010) was used to prepare NLPs of a variety of defined size populations. Using the Malvern Laser Light Scattering instrument (Zetasizer 1000) nascent populations of NLP were measured to be 9 nm. To prepare NLP populations with Erythromycin of defined sizes the following procedure was followed: A stock solution (150 ml) of Erythromycin 1 mg/ml was prepared by addition of Erythromycin into 150 ml of distilled water. The solution was solubilized by stirring at room temperature for 5 minutes. 1 ml aliquots of NLP starting materials were placed in 10 ml test tubes. To prepare defined populations of NLP product incorporating Erythromycin various amounts of ethanol were added to each of the sample preparations. Following formation of the NLP preparations, 1 ml aliquots of each sample were added to 20 ml of the prepared Erythromycin stock solution in water 1 mg/ml using a 2 ml pipette. Each preparation was stirred at room temperature for 5 minutes and then 2 ml aliquots were removed, vortexed for 20 seconds and then subjected to size analysis using the Malvern Laser Light Scattering instrument. Results are shown in Table 3.

TABLE 3

| Stock Precursor Solution | Ethanol | Erythromycin | Size |
|---|---|---|---|
| 1 ml | 0 ml | [Control] | 289 nm |
| 1 ml | 0.5 ml | [NLP Assembly] | 162 nm |
| 1 ml | 1.0 ml | [NLP Assembly] | 141 nm |
| 1 ml | 2.0 ml | [NLP Assembly] | 105 nm |
| 1 ml | 5.0 ml | [NLP Assembly] | 66 nm |
| 1 ml | 10.0 ml | [NLP Assembly] | 52 nm |

Example 4

NLPs with Both Lipid and Water Soluble Passenger Molecules

Shelf-Stable Precursor Solution (Manufacturing Lot 0013-040010) was used to prepare NLPs of a variety of defined size populations. Using the Malvern Laser Light Scattering instrument nascent populations of NLP were measured to be 9 nm. To prepare NLP populations with both Vitamin B12 (water soluble) and Vitamin K1 (lipid soluble) of defined sizes the following procedure was followed: A stock solution (70 ml) of Vitamin B12 1 mg/ml was prepared by addition of 70 mg of Vitamin B12 into 70 ml of distilled water. The solution was solubilized by stirring at room temperature for 5 minutes. A preparation of Vitamin K1 loaded NLPs were prepared by solubilization of 10 mg of Vitamin K1 into 10 ml of Shelf-Stable Precursor Solution Manufacturing Lot 0013-040010). 1 ml aliquots of NLP loaded with Vitamin K1 were placed in 10 ml test tubes. To prepare defined populations of NLP product incorporating both Vitamin K1 and Vitamin B12 various amounts of ethanol were added to each of the sample preparations. Following formation of the NLP preparations, 0.5 ml aliquots of each sample were added to 10 ml of the prepared Vitamin B12 stock solution in water 1 mg/ml using a 2 ml pipette. Each preparation was stirred at room temperature for 5 minutes and then 2 ml aliquots were removed, vortexed for 20 seconds and then subjected to size analysis using the Malvern Laser Light Scattering instrument. The results obtained are shown in Table 4.

TABLE 4

| Stock Precursor Solution | Ethanol | Vitamins K1 and B12 | Size |
|---|---|---|---|
| 1 ml | 0 ml | [Control] | 217 nm |
| 1 ml | 0.5 | [NLP Assembly] | 122 nm |
| 1 ml | 1.0 | [NLP Assembly] | 94 nm |
| 1 ml | 2.0 | [NLP Assembly] | 71 nm |
| 1 ml | 5.0 | [NLP Assembly] | 68 nm |
| 1 ml | 10.0 | [NLP Assembly] | 57 nm |

Example 5

Preparation of Defined Populations—Effect of Solvent

Shelf-Stable Precursor Solution (Lot number 0013-040100) was used as starting stock for production of NLP assemblies Various amounts and types of solvent were added to the starting stock to make solvent diluted stock solutions. NLP assemblies were prepared by converting the solvent diluted stock solutions by addition of 1 ml thereof into 20 ml of distilled water while stirring, using a mixing plate and stir bar at room temperature. The mixture was stirred for 5 minutes, vortexed gently for 20 seconds, and placed into a sample cuvet which was used to determine the size of the resulting NLP assembly population with a Malvern 1000 Zetasizer™ laser light scattering instrument set to evaluate particle size using multimodal analysis.

In addition the size of the native NLPs present in the precursor were also determined by examining the precursor alone using the Malvern 1000 with settings as already described.

The data in Table 5 demonstrates that various solvents may be used to form NLP assemblies or NLPs. While Ethanol will likely be chosen for many applications due to it relatively non-toxic properties, it may be desirable to use other solvents for particular NLP characteristics.

TABLE 5

| Stock Precursor Solution A (mls) | Solvent Amount B Added to A (mls) | Water Amount Added to 1 ml of A + B (mls) | Ethanol Solvent Size (nm) | Methanol Solvent Size (nm) | 1-Propanol Solvent Size (nm) | 2-Propanol Solvent Size (nm) |
|---|---|---|---|---|---|---|
| 1 | 0 | 0 | 14 | 14 | 14 | 14 |
| 1 | 0 | 20 | 240 | 240 | 240 | 240 |
| 1 | 0.5 | 20 | 133 | 191 | 112 | 95 |
| 1 | 1 | 20 | ND | ND | ND | 46 |
| 1 | 2 | 20 | 108 | 97 | 66 | 13 |
| 1 | 5 | 20 | 49 | 60 | 23 | ND |
| 1 | 10 | 20 | 25 | 43 | ND | ND |

TABLE 5-continued

| Stock Precursor Solution A (mls) | Solvent Amount B Added to A (mls) | Water Amount Added to 1 ml of A + B (mls) | Ethanol Solvent Size (nm) | Methanol Solvent Size (nm) | 1-Propanol Solvent Size (nm) | 2-Propanol Solvent Size (nm) |
|---|---|---|---|---|---|---|

Example 6

Use of Heating to Control Size

NLP assemblies and ECVs which have been prepared by secondary addition of solvent to precursor solution such as in Example 5 may be heated to further reduce (in a controlled manner) the average size thereof.

NLP assemblies and ECVs were produced using Stock Precursor Solution (Lot number 0013-040010) which contained native NLPs sized at approximately 10 nanometers (as measured using the Malvern 1000 Zetasizer laser Light Scattering Instrument with sizing for particle populations set to multimodal setting).

Dilutions with ethanol were made of the control and test portions as indicated in Table 6 to form solvent diluted stock solutions. NLP assemblies and ECVs were prepared by converting the solvent diluted stock solutions by addition of 1 ml thereof to 20 ml of distilled water while stirring, using a mixing plate and stir bar at room temperature as described in Example 5. One portion was retained as a control, and one portion was removed for testing of the determination of the effect of heating on the NLP assembly population or ECV population.

Heating of the test portion was accomplished by placing five ml samples into a test tube which was then lowered into rapidly boiling water for 3 minutes. The tubes containing the thus-heated samples were removed from boiling water and allowed to cool to room temperature, then vortexed gently for 20 seconds. The control was treated in the same way with the exception that it was not heated.

An aliquot of each portion (control and heated) was transferred into a sample cuvet which was used to determine the size of the resulting NLP assembly population with a Malvern 1000 Zetasizer™ laser light scattering instrument set to evaluate particle size using multimodal analysis.

TABLE 6

| Stock Precursor Solution A (mls) | Ethanol B (mls) | Water (Added to 1 ml of A + B) (mls) | Size (nm) No Heating | Size (nm) With Heating | % Reduction with Heating |
|---|---|---|---|---|---|
| 1 | 0 | 0 | 10 | 10 | 0 |
| 1 | 0 | 20 | 252 | 158 | 37.3 |
| 1 | 0.5 | 20 | 188 | 125 | 33.5 |
| 1 | 2 | 20 | 138 | 96 | 30.4 |
| 1 | 5 | 20 | 57 | 35 | 38.6 |
| 1 | 10 | 20 | 36 | 26 | 31 |

The results of these evaluations demonstrate that heating of NLP assemblies or ECVs reduced the size of resulting carrier vehicles in a controlled manner with an average reduction of 34%. Because these withstand heat, it is possible to not only reduce the size of the NLPs but to use heating and sterilizing techniques such as flash pasteurization, which is desirable in the food and beverage industry to control the bacterial load. This can be conducted at temperatures up to about 220 degrees Fahrenheit with the usual range of about 180 to 220 degrees Fahrenheit.

Example 8

Masking the Taste of Lidocaine Hydrochloride

Encapsulating particles were prepared using Shelf-Stable Precursor Stock (Lot Number 0013-050015). The size of native NLPs in this precursor stock was determined to be 8.1 nm using the Malvern 1000 Zetasizer Laser Light Scattering Instrument set to analyze size populations using multimodal analysis mode. To 5 ml of stock was added 50 mg of Lidocaine Hydrochloride. The mixture was vortexed until the Lidocaine Hydrochloride was dissolved into the stock, forming preloaded NLPs. Ethanol was added to the preloaded NLPs as indicated below to form solvent diluted NLP stock. One ml of solvent diluted NLP stock was further diluted by addition to 20 ml of distilled water while stirring using mixing plate and stir bar at room temperature. The resulting carrier vehicles were stirred for 5 minutes and vortexed gently for 20 seconds and placed into a sample cuvet which was used to determine the size of the resulting population with a Malvern 1000 Zetasizer™ laser light scattering instrument set to evaluate particle size using multimodal analysis.

TABLE 8

| NLP stock A (mls) | Ethanol B mls) | Water (Added to 1 ml of A + B) (mls) | Preloaded with Lidocaine Hydrochloride? | Size (nm) |
|---|---|---|---|---|
| 1 | 0 | 0 | No | 8.1 |
| 1 | 0 | 20 | No | 262 |
| 1 | 0 | 20 | Yes | 276 |
| 1 | 0.5 | 20 | Yes | 91 |
| 1 | 1 | 20 | Yes | 88 |
| 1 | 2 | 20 | Yes | 68 |
| 1 | 5 | 20 | Yes | 46 |

The size of the native NLPs present in the stock precursor was determined by examining the precursor alone using the Malvern 1000 with settings as already described.

The preparations of carrier vehicles formed using the Preloaded NLPs with Lidocaine Hydrochloride masked the taste of the Lidocaine Hydrochloride.

Example 9

Caffeine as a Passenger Molecule

Carrier vehicle preparations were made using caffeine as the passenger molecule. Two concentrations were evaluated for the ability to mask taste and for stability over time both in size and in taste masking capability.

A Preloaded NLPs stock preparation was prepared. First, 5 g of caffeine was dissolved into 100 ml of distilled water. Separately, 10 ml of Shelf stable precursor solution (Lot number 0013-010007), which contained native NLPs measured at 12 nm using the Malvern 1000 Zetasizer Laser Light Scattering Instrument with analysis mode set to multimodal population setting, was diluted with 10 ml of Ethanol as a secondary solvent (1:1 Volume/Volume dilution). This formed solvent diluted NLP stock. The solvent diluted NLP stock was added to the 100 ml solution containing 5 grams of caffeine while the solution was being stirred at room temperature. The entire 120 ml preparation thus prepared was added into 880 ml of distilled water while stirring at room temperature for 5 minutes. A 3 ml sample was removed for analysis and vortexed gently for 20 seconds. The carrier vehicles loaded with caffeine as a passenger molecule were placed into a sample cuvet which was used to determine the size of the resulting carrier vehicle population with a Malvern 1000 Zetasizer™ laser light scattering instrument set to evaluate particle size using multimodal analysis. The carrier vehicles were determined to be 121 nm.

When the sample was evaluated for taste masking, the bitter taste of the caffeine was masked. In addition, the final preparation of carrier vehicles loaded with caffeine was optically clear.

It was concluded that this procedure could be used for applications calling for optically clear products suitable for oral consumption such as beverages or medicinal preparations. Bitter or otherwise objectionable passenger molecules thus encapsulated in carrier vehicles could be consumed without the consumer having to taste the passenger molecule. In addition to caffeine, it is contemplated that electrolytes (NaCl and KCl) and vitamins among other passenger molecules would be appropriate candidates for formulation as described in Example 8.

Example 10

Production of Preloaded NLP Preparations Containing Caffeine

Preloaded NLPs were prepared from Shelf-Stable Precursor stock (Lot Number 0013-050015). The size of the nascent NLPs was determined to be 8 nm using the Malvern 1000 Zetasizer Laser Light Scattering Instrument set to analyze size populations using multimodal analysis mode. The preparation containing caffeine was prepared as follows:

1. Anhydrous Caffeine (2.5 g) was dissolved into 50 ml of distilled water at room temperature
2. To 20 ml of Precursor Stock was added 10 ml of ethanol.
3. Material from step 2 was added to caffeine solution from step 1 while stirring at room temperature. The mixture was stirred for 5 minutes. This resulted in the production of preloaded NLPs containing caffeine at 31.3 mg/ml.
4. The finished product containing caffeine at 0.5 mg/ml was produced by mixing preparation from step 3 into an appropriate volume of distilled water (1:62.5 volume/volume)
5. The size of the finished preparation was determined using the Malvern 1000 Zetasizer Laser Light Scattering Instrument set to analyze populations using multimodal analysis mode. The size of the finished preparation was determined to be 147 nm. The finished preparation containing 0.5 mg/ml caffeine was optically clear.
6. The finished preparation from step 5 was evaluated for its ability to mask the taste of caffeine by placing 1 ml of preparation into mouth. The preparation was found to effectively mask the taste of caffeine.

Example 11

Production of Preloaded NLP Preparations Containing Lipid Soluble Vitamins as a Means to Produce Finished Products of Small Size and Ability to Mask Adverse Taste of Lipid Soluble Vitamins Preloaded NLPs were prepared from Shelf-Stable Precursor Stock (Lot Number 0013-050015). The size of the nascent NLPs was determined to be 8 nm using the Malvern 1000 Zetasizer Laser Light Scattering Instrument set to analyze size populations using multimodal analysis mode. The preparation containing lipid soluble vitamins was prepared as follows:

1. Solvent diluted precursor stock was prepared by adding 20 ml of ethanol to 40 ml of shelf stable precursor stock.
2. 250 mg of Vitamin D3 DSM Chemicals), 500 mg of Vitamin E (DSM Chemicals) and 4 mg of Vitamin K (DSM Chemicals) were dissolved in the preparation resulting from step one. This was stirred at room temperature and resulted in a preloaded NLP population.
3. The preloaded NLP preparation from step 2 was diluted 1 to 50 into distilled water to yield a finished product suitable for oral consumption containing the recommended daily allowance ("RDA") of the 3 lipid soluble vitamins.
4. The size of the finished preparation was determined using the Malvern 1000 Zetasizer Laser Light Scattering Instrument set to analyze populations using multimodal analysis mode. The size of the finished preparation was determined to be 168 nm.
5. The finished preparation from step 5 was evaluated for its ability to mask the taste of offensive taste of the three lipid soluble vitamins by placing 1 ml into the mouth. The preparation was found to effectively mask the taste of all three lipid soluble vitamins; Vitamin D3, E and K.

I claim:

1. NLPs (Nanolipidic Particles) comprising particles formed from a hydrous monophasic precursor solution having phospholipids, water, and a non-aqueous solvent selected from the group consisting of ethanol, 1-propanol, and 2-propanol, said hydrous monophasic precursor solution having been diluted by one or more sequential dilutions of non-aqueous solvent resulting in a solvent-diluted precursor solution, and then dilution of said solvent-diluted precursor solution with an aqueous solvent to yield said NLPs sized from about 1 nm to about 20 nm, said NLPs being self-stabilizing at this size range by the retention of said aqueous solvent in said NLPs, said NLPs further retaining a concentration of said non-aqueous solvent from about 0.5% to about 14%.

2. The NLPs of claim 1, wherein the NLPs are sized from about 6 to about 12 nm.

3. The NLPs of claim 1, wherein said non-aqueous solvent is ethanol.

4. The NLPs of claim 1, wherein said phospholipids are selected from the group consisting of phosphatidyl choline (PC), phospatidylethanolamine (PE), phosphatidic acid (PA) and phosphatidylinositol (PI), and mixtures thereof.

5. The NLPs of claim 1, wherein said non-aqueous solvent is ethanol, and said phospholipids are selected from the group consisting of phosphatidyl choline (PC), phospatidylethanolamine (PE), phosphatidic acid (PA) and phosphatidylinositol (PI), and mixtures thereof.

6. The NLPs of claim 5, wherein the NLPs are sized from about 6 to about 12 nm.

7. The NLPs of claim 1, wherein said NLPs are for oral consumption.

8. The NLPs of claim 5, wherein said NLPs are for oral consumption.

9. The NLPs of claim 1, wherein said NLPs are for topical application.

10. The NLPs of claim 5, wherein said NLPs are for topical application.

11. Nanolipidic Particles (NLPs) having a passenger molecule, said NLPs comprising particles formed from a hydrous monophasic precursor solution having phospholipids, water, and a non-aqueous solvent selected from the group consisting of ethanol, 1-propanol, and 2-propanol, said hydrous monophasic precursor solution having been diluted by one or more sequential dilutions of non-aqueous solvent resulting in a solvent-diluted precursor solution having said NLPs sized from about 1 nm to about 20 nm, and then said solvent diluted-precursor solution being diluted with an aqueous solvent, said NLPs being stabilized for at least two years at this size range by the retention of said aqueous solvent in said NLPs, said NLPs further retaining a concentration of said non-aqueous solvent from about 0.5% to about 14%, with a passenger molecule encapsulated therein.

12. The NLPs of claim 11, wherein said non-aqueous solvent is ethanol.

13. The NLPs of claim 11, wherein said phospholipids are selected from the group consisting of phosphatidyl choline (PC), phospatidylethanolamine (PE), phosphatidic acid (PA) and phosphatidylinositol (PI), and mixtures thereof.

14. The NLPs of claim 11, wherein the NLPs are sized from about 6 to about 12 nm.

15. The NLPs of claim 11, wherein said NLPs are for oral consumption.

16. The NLPs of claim 11, wherein said NLPs are for topical application.

17. The NLPs of claim 11, wherein said non-aqueous solvent is ethanol, and said phospholipids are selected from the group consisting of phosphatidyl choline (PC), phospatidylethanolamine (PE), phosphatidic acid (PA) and phosphatidylinositol (PI), and mixtures thereof.

18. The NLPs of claim 17, wherein said NLPs are for oral consumption.

19. The NLPs of claim 17, wherein said NLPs are for topical application.

20. Nanolipidic Particles (NLPs), said NLPs comprising particles formed from a hydrous monophasic precursor solution having phospholipids, water, and a non-aqueous solvent selected from the group consisting of ethanol, 1-propanol, and 2-propanol, said hydrous monophasic precursor solution having been diluted by one or more sequential dilutions of non-aqueous solvent and then at least one dilution of aqueous solvent yielding said NLPs sized from about 6 nm to about 12 nm, said NLPs having a retention of said aqueous solvent in said NLPs, said NLPs further retaining a concentration of said non-aqueous solvent from about 0.5% to about 14%.

21. The NLPs of claim 20, wherein said non-aqueous solvent is ethanol.

22. The NLPs of claim 20, wherein said phospholipids are selected from the group consisting of phosphatidyl choline (PC), phospatidylethanolamine (PE), phosphatidic acid (PA) and phosphatidylinositol (PI), and mixtures thereof.

23. The NLPs of claim 20, wherein said NLPs are for oral consumption.

24. The NLPs of claim 20, wherein said NLPs are for topical application.

25. The NLPs of claim 20, wherein said non-aqueous solvent is ethanol, and said phospholipids are selected from the group consisting of phosphatidyl choline (PC), phospatidylethanolamine (PE), phosphatidic acid (PA) and phosphatidylinositol (PI), and mixture thereof.

26. The NLPs of claim 25, wherein said NLPs are for oral consumption.

27. The NLPs of claim 25, wherein said NLPs are for topical application.

28. NLPs (Nanolipidic Particles) comprising particles formed from a hydrous monophasic precursor solution having phospholipids, water, and a non-aqueous solvent selected from the group consisting of ethanol, 1-propanol, and 2-propanol, said hydrous monophasic precursor solution having been diluted by one or more sequential dilutions of non-aqueous solvent, and then at least one dilution with aqueous solvent, said dilutions yielding NLPs stably sized from 1 nm to 20 nm, said NLPs retaining said aqueous solvent in said NLPs ranging from a 1:1 to 20:1 ratio of water to phospholipids, said NLPs further retaining having a concentration of said non-aqueous solvent from about 0.5% to about 14%.

29. The NLPs of claim 28, wherein the NLPs are sized from 6 nm to 12 nm.

30. The NLPs of claim 28, wherein said non-aqueous solvent is ethanol.

31. The NLPs of claim 28, wherein said phospholipids are selected from the group consisting of phosphatidyl choline (PC), phospatidylethanolamine (PE), phosphatidic acid (PA) and phosphatidylinositol (PI), and mixture thereof.

32. The NLPs of claim 28, wherein said non-aqueous solvent is ethanol, and said phospholipids are selected from the group consisting of phosphatidyl choline (PC), phospatidylethanolamine (PE), phosphatidic acid (PA) and phosphatidylinositol (PI), and mixtures thereof.

33. The NLPs of claim 28, wherein a passenger molecule is encapsulated within said NLPs.

34. NLPs (Nanolipidic Particles) comprising particles formed by a plurality of sequential dilutions of a hydrous monophasic precursor solution, said hydrous monophasic precursor consisting essentially of phospholipids, water and a non-aqueous solvent selected from the group containing ethanol, 1-propanol and 2-propanol, and said sequential dilution including one or more dilutions with a non-aqueous solvent and then at least one dilution with an aqueous solvent, yielding NLPs stably sized from 1 nm to 20 nm, said NLPs self-stabilizing at this size range by the incorporation and retention of said aqueous solvent in said NLPs, said NLPs further retaining a concentration of non-aqueous solvent from about 0.5% to about 14%, and said NLPs are independently shelf-stable at least two years.

35. The NLPs of claim 34, wherein the NLPs are sized from 6 nm to 12 nm.

36. The NLPs of claim 34, wherein said non-aqueous solvent is ethanol.

37. The NLPs of claim 33, wherein said phospholipids are selected from the group consisting of phosphatidyl choline (PC), phospatidylethanolamine (PE), phosphatidic acid (PA) and phosphatidylinositol (PI), and mixture thereof.

38. The NLPs of claim 34, wherein said non-aqueous solvent is ethanol, and said phospholipids are selected from the group consisting of phosphatidyl choline (PC), phospatidylethanolamine (PE), phosphatidic acid (PA) and phosphatidylinositol (PI), and mixtures thereof.

39. The NLPs of claim 34, wherein a passenger molecule is encapsulated within said NLPs.

* * * * *